(12) United States Patent
Sakai

(10) Patent No.: US 9,961,270 B2
(45) Date of Patent: May 1, 2018

(54) IMAGING SYSTEM AND PROCESSING DEVICE

(71) Applicant: OLYMPUS CORPORATION, Tokyo (JP)

(72) Inventor: Aiko Sakai, Kodaira (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days. days.

(21) Appl. No.: 15/627,503

(22) Filed: Jun. 20, 2017

(65) Prior Publication Data

US 2017/0302837 A1 Oct. 19, 2017

Related U.S. Application Data

(63) Continuation of application No. PCT/JP2016/077853, filed on Sep. 21, 2016.

(30) Foreign Application Priority Data

Oct. 1, 2015 (JP) .................................. 2015-195803

(51) Int. Cl.
*G03B 15/03* (2006.01)
*H04N 5/235* (2006.01)
(Continued)

(52) U.S. Cl.
CPC ....... *H04N 5/2351* (2013.01); *A61B 1/00013* (2013.01); *A61B 1/0661* (2013.01); *A61B 2034/301* (2016.02)

(58) Field of Classification Search
USPC .................................................. 396/17, 164
See application file for complete search history.

(56) References Cited

U.S. PATENT DOCUMENTS

| 5,049,997 A | * | 9/1991 | Arai | ..................... H04N 5/2351 348/364 |
| 6,181,379 B1 | * | 1/2001 | Kingetsu | ............ H04N 1/00286 348/205 |

(Continued)

FOREIGN PATENT DOCUMENTS

| JP | H11-261994 A | 9/1999 |
| JP | 2000-047119 A | 2/2000 |

(Continued)

OTHER PUBLICATIONS

International Search Report dated Nov. 8, 2016 issued in PCT/JP2016/077853.

*Primary Examiner* — Clayton E Laballe
*Assistant Examiner* — Warren K Fenwick
(74) *Attorney, Agent, or Firm* — Scully, Scott, Murphy & Presser, P.C.

(57) ABSTRACT

An imaging system includes: an imaging unit configured to capture an image in a temporally continuous manner; a change rate setting unit configured to variably set a change rate of brightness of image continuously captured by the imaging unit; a parameter setting unit configured to be capable of variably setting a light adjustment parameter for altering the change rate of the brightness of the image such that the change rate set by the change rate setting unit is obtained; a photometry unit configured to acquire a photometric value indicating the brightness of the image; and a light adjustment unit configured to generate, based on the photometric value, a light adjustment control signal in line with a light adjustment profile for causing the photometric value to reach a predetermined target value of the brightness within a certain time period.

9 Claims, 9 Drawing Sheets

(51) Int. Cl.
  *A61B 1/00*  (2006.01)
  *A61B 1/06*  (2006.01)
  *A61B 34/30*  (2016.01)

(56) References Cited

U.S. PATENT DOCUMENTS

| | | | | |
|---|---|---|---|---|
| 6,239,840 | B1 * | 5/2001 | Shibuya | H04N 5/2351 348/297 |
| 6,464,633 | B1 * | 10/2002 | Hosoda | A61B 1/0638 348/68 |
| RE38,771 | E * | 8/2005 | Shibuya | H04N 5/2351 348/221.1 |
| 7,136,098 | B1 * | 11/2006 | Burnett | H04N 5/2256 348/230.1 |
| 7,865,033 | B2 * | 1/2011 | Han | G06T 5/009 348/353 |
| 7,876,370 | B2 * | 1/2011 | Hirai | H04N 5/217 348/222.1 |
| 2014/0180004 | A1 * | 6/2014 | Yamashita | A61B 1/0638 600/109 |
| 2014/0371535 | A1 * | 12/2014 | Seto | A61B 1/0661 600/160 |

FOREIGN PATENT DOCUMENTS

| | | |
|---|---|---|
| JP | 2000-347112 A | 12/2000 |
| JP | 2009-273577 A | 11/2009 |
| JP | 2010-194001 A | 9/2010 |
| JP | 2013-052022 A | 3/2013 |
| WO | WO 2014/021022 A1 | 2/2014 |

* cited by examiner

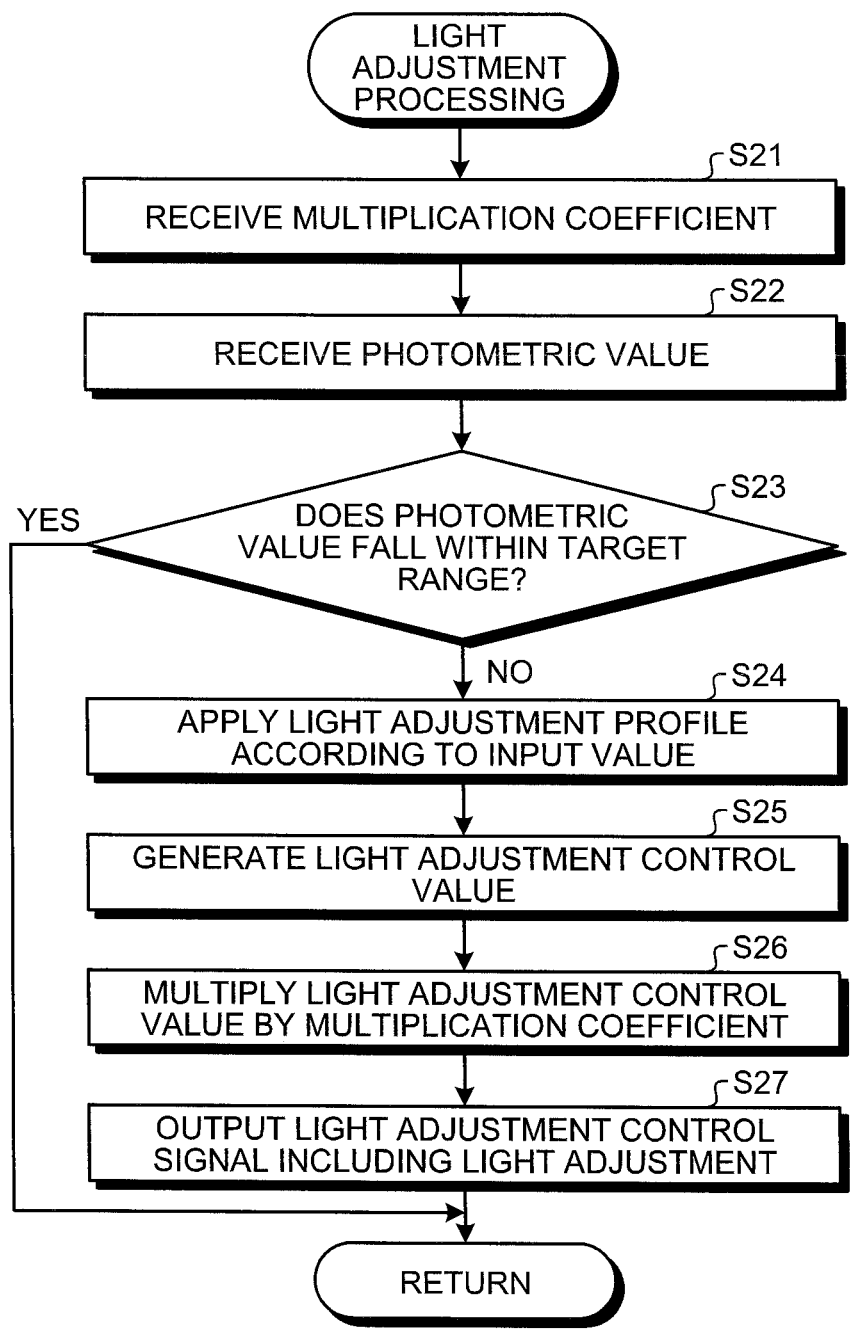

IMAGING SYSTEM AND PROCESSING DEVICE

CROSS REFERENCES TO RELATED APPLICATIONS

This application is a continuation of PCT international application Ser. No. PCT/JP2016/077853 filed on Sep. 21, 2016 which designates the United States, incorporated herein by reference, and which claims the benefit of priority from Japanese Patent Applications No. 2015-195803, filed on Oct. 1, 2015, incorporated herein by reference.

BACKGROUND

The present disclosure relates to an imaging system and a processing device.

An endoscope system has been used in a medical field in the past to observe the inside of a subject. Typically, the endoscope captures an in-vivo image by inserting an insertion portion having an elongated shape into the subject such as a patient to exit illumination light supplied by a light source device through a distal end of this insertion portion and then receive reflected light of this illumination light using an image sensor. A processing device (processor) of the endoscope system applies predetermined image processing to the in-vivo image captured by the image sensor of the endoscope. Thereafter, this in-vivo image is presented on a display of the endoscope system. A user such as a medical doctor observes an organ of the subject based on the in-vivo image presented on the display.

In the related art, in order to obtain brightness of an image reaching target brightness, the processor detects the brightness of an image captured by the endoscope and automatically carries out light adjustment processing to control a light source based on the detected brightness of the image. Incidentally, there is a request from a user for personally setting a change rate of the brightness of an image. In order to respond to this request, an endoscope system provided with a plurality of photometric circuits and having a function to switch the photometric circuits in agreement with the change rate of the brightness of the image set by the user has been suggested (for example, refer to JP 2000-347112 A).

DISCLOSURE

According to the configuration disclosed in JP 2000-347112 A, however, a complicated configuration has been required to provide the plurality of photometric circuits within the processor and besides, difficult control processing has been also necessary since the switching of the plurality of photometric circuits to any one thereof is controlled.

SUMMARY

An imaging system according to one aspect of the present disclosure includes: an imaging unit configured to capture an image in a temporally continuous manner; a change rate setting unit configured to variably set a change rate of brightness of image continuously captured by the imaging unit; a parameter setting unit configured to be capable of variably setting a light adjustment parameter for altering the change rate of the brightness of the image such that the change rate set by the change rate setting unit is obtained; a photometry unit configured to acquire a photometric value indicating the brightness of the image captured by the imaging unit; and a light adjustment unit configured to generate, based on the photometric value input from the photometry unit, a light adjustment control signal in line with a light adjustment profile for causing the photometric value input from the photometry unit to reach a predetermined target value of the brightness of the image captured by the imaging unit within a certain time period, wherein the parameter setting unit sets a deemed photometric value as the light adjustment parameter, and the photometry unit selects one of the photometric value and the deemed photometric value as an input value of the photometric value based on a comparison result between the deemed photometric value set by the parameter setting unit and the photometric value acquired by the photometry unit, and outputs the light adjustment control signal based on the input value and the light adjustment profile.

An imaging system according to another aspect of the present disclosure includes: an imaging unit configured to capture an image in a temporally continuous manner; a change rate setting unit configured to variably set a change rate of brightness of image continuously captured by the imaging unit; a parameter setting unit configured to a light adjustment parameter for altering the change rate of the brightness of the image by using a change rate coefficient according to the change rate set by the change rate setting unit; a photometry unit configured to acquire a photometric value indicating the brightness of the image captured by the imaging unit; and a light adjustment unit configured to multiply a value of the light adjustment control signal generated in line with a light adjustment profile for causing the photometric value input from the photometry unit to reach a predetermined target value of the brightness of the image captured by the imaging unit within a certain time period, by the change rate coefficient set by the parameter setting unit, to output based on the photometric value input form the photometry unit.

A processing device for processing an image captured by an imaging unit in a temporally continuous manner according to the present disclosure includes: a change rate setting unit configured to variably set a change rate of brightness of an image continuously captured by the imaging unit; a parameter setting unit configured to be capable of variably setting a light adjustment parameter for altering the change rate of the brightness of the image such that the change rate set by the change rate setting unit is obtained; a photometry unit configured to acquire a photometric value indicating the brightness of the image captured by the imaging unit; and a light adjustment unit configured to generate, based on the photometric value input from the photometry unit, a light adjustment control signal in line with a light adjustment profile for causing the photometric value input from the photometry unit to reach a predetermined target value of the brightness of the image captured by the imaging unit within a certain time period, wherein the parameter setting unit sets a deemed photometric value as the light adjustment parameter, and the photometry unit selects one of the photometric value and the deemed photometric value as an input value of the photometric value based on a comparison result between the deemed photometric value set by the parameter setting unit and the photometric value acquired by the photometry unit, and outputs the light adjustment control signal based on the input value and the light adjustment profile.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 9 is a flowchart illustrating processing procedures of light adjustment processing carried out by a light adjustment unit illustrated in FIG. 8.

DETAILED DESCRIPTION

Figure 1:
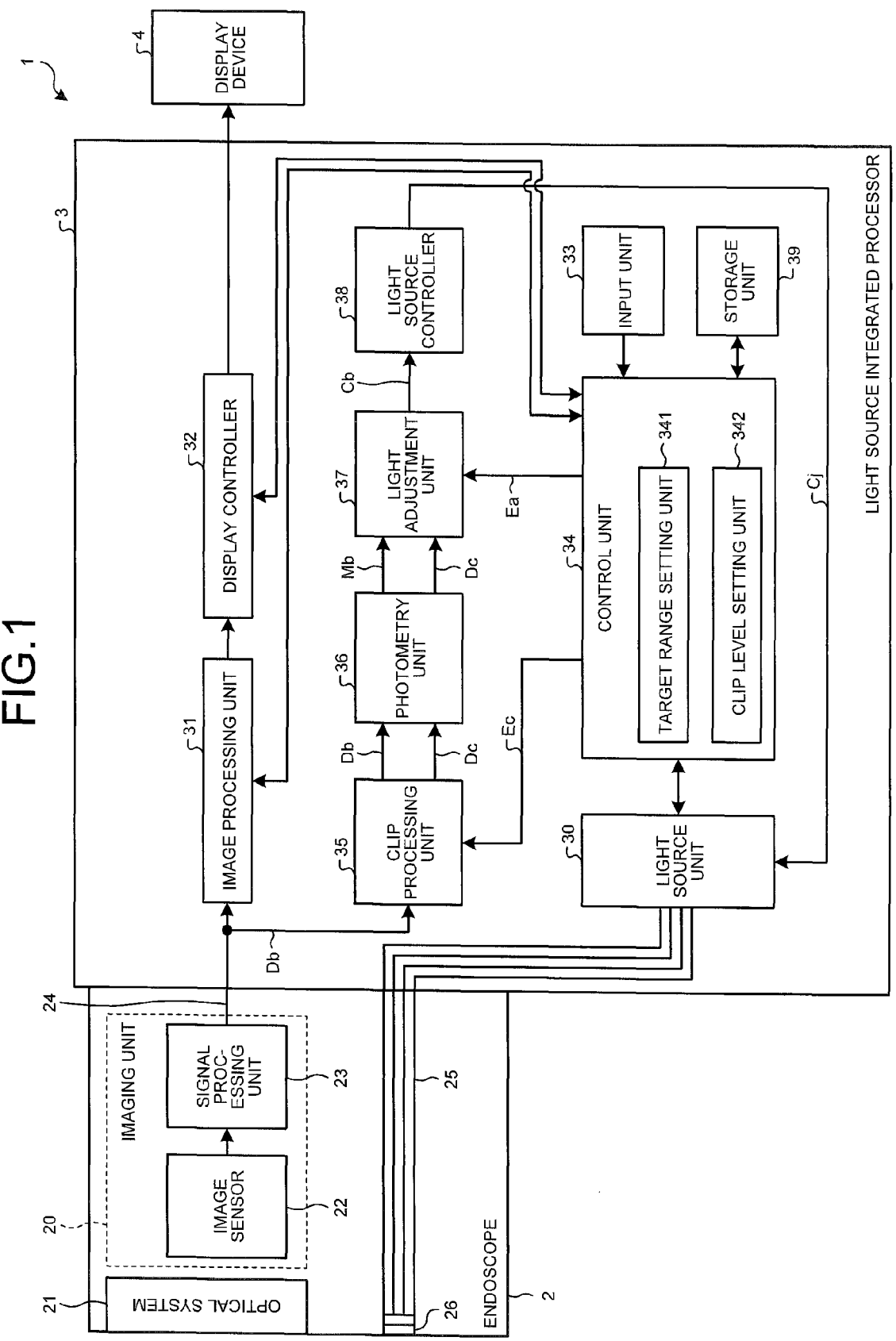
FIG. 1 is a schematic diagram illustrating an overview configuration of an endoscope system according to a first embodiment of the disclosure.

In the following explanation, an endoscope system for medical use will be described as modes for carrying out the disclosure (hereinafter, referred to as "embodiments"). The embodiments are not construed to limit the disclosure. Additionally, in the descriptions of the drawings, similar portions are given similar reference numerals.

First Embodiment

FIG. 1 is a schematic diagram illustrating an overview configuration of an endoscope system according to a first embodiment of the disclosure.

As illustrated in FIG. 1, an endoscope system 1 (imaging system) according to the first embodiment includes an endoscope 2 (imaging device) with flexibility to be put into a subject, a light source integrated processor 3 (processing device) that carries out predetermined image processing on an image signal sent from the endoscope 2 mounted thereon via a connector (not illustrated), and a display device 4 that displays an in-vivo image corresponding to the image signal to which the light source integrated processor 3 has applied the image processing. The light source integrated processor 3 is configured in such a manner that the endoscope 2 is electrically and optically connected thereto so as to be freely attached and detached. The light source integrated processor 3 supplies illumination light to the endoscope 2.

The endoscope 2 has an insertion portion to be inserted into the subject. An imaging unit 20 provided at a distal end portion of the insertion portion generates the image signals for the inside of the subject by capturing the interior of the body of the subject in a temporally continuous manner. The endoscope 2 includes an optical system 21, the imaging unit 20, an illumination lens 26 provided at a distal end portion, an electric cable 24 of which a distal end is connected to the imaging unit 20 and of which a proximal end extends to the connector, and an illumination fiber (light guide cable) 25 extending from the distal end portion of the endoscope 2 until a proximal end thereof reaches the connector. The endoscope 2 also has an operation switch unit (not illustrated) on which various operation switches are provided. The illumination lens 26 is provided on a distal end side of the light guide cable 25 such that an object is irradiated with light supplied from the light source integrated processor 3 through the illumination lens 26. The imaging unit 20 includes an image sensor 22 and a signal processing unit 23.

The optical system 21 is constituted using one lens or a plurality of lenses and provided at a former stage of the image sensor 22 to form an image of incident light from the object. The optical system 21 may have an optical zoom function to vary an angle of view and a focus function to vary a focal point.

The image sensor 22 captures an optical image formed by the optical system 21 to generate the image signal. The image sensor 22 may include an electronic shutter function such that an exposure period may be altered under the control of the light source integrated processor 3. The image sensor 22 is, for example, a CMOS image sensor or a CCD image sensor, in which a plurality of pixels that receive light from the object irradiated with light and then photoelectrically convert the received light to generate the image signal is arranged on a light-receiving surface in a matrix form.

The signal processing unit 23 has an analog processing unit that carries out noise removal processing and clamp processing on the image signal (analog) output from the image sensor 22 and an A/D converter that carries out A/D conversion processing, to output the image signal (digital) to an image processing unit 31 (described later) of the light source integrated processor 3. The signal processing unit 23 outputs a luminosity signal Db including a luminosity level of the image captured by the image sensor 22 to a clip processing unit 35 (described later) of the light source integrated processor 3. The luminosity level represents an amount of brightness of the image. Note that the signal processing unit 23 may output the image signal (digital) to the clip processing unit 35. In addition, a configuration with the signal processing unit 23 provided in the light source integrated processor 3 is also considered.

The illumination lens 26 is positioned at a distal end of the light guide cable 25. While the endoscope 2 is optically mounted on the light source integrated processor 3, the object is irradiated with light emitting from a light source unit 30 (described later) through the illumination lens 26 located at a distal end of the endoscope 2 by way of the light guide cable 25.

The endoscope 2 is mounted on the light source integrated processor 3 so as to be freely attached and detached, whereby the light source integrated processor 3 applies the predetermined image processing to the image signal sent from the mounted endoscope 2 and then generates the in-vivo image. The light source integrated processor 3 outputs the acquired in-vivo image to the display device 4 to display thereon.

The light source integrated processor 3 includes the light source unit 30, the image processing unit 31, a display controller 32, an input unit 33 (change rate setting unit), a control unit 34, the clip processing unit 35, a photometry unit 36, a light adjustment unit 37, a light source controller 38 (alteration unit), and a storage unit 39.

The light source unit 30 supplies the illumination light to the endoscope 2. The object is irradiated with light emitting from the light source unit 30 through the illumination lens 26 located at the distal end of the endoscope 2 by way of the light guide cable 25 of the endoscope 2. The light source unit 30 has, for example, a light source such as a white LED and a light source driver configured to supply electric power to the light source, thereby supplying white light to the endoscope 2.

The image processing unit 31 applies the predetermined image processing to the image signal acquired by the image sensor 22 of the endoscope 2. The image processing unit 31 carries out, for example, optical black (OB) subtraction processing, demosaicing processing, white balance (WB) adjustment processing, electronic zoom processing, edge emphasis processing, mask processing, and on-screen display (OSD) processing on the image signal (digital) output from the signal processing unit 23 and thereafter, outputs the acquired image signal.

The display controller 32 converts the image signal acquired by the image processing unit 31 to a format allowing the display device 4 to display and output and then causes the display device 4 to display. The display controller 32 includes a converter from a digital signal to an analog signal (DAC) and an encoder to convert the image signal input from the image processing unit 31 to, for example, an analog signal from a digital signal and then alter the image signal converted to the analog signal to a format such as a high-vision mode to output to the display device 4.

The input unit 33 accepts input of various types of instruction information and inputs the various types of instruction information that have been accepted to the control unit 34. The input unit 33 accepts input of setting information variably setting the change rate of the brightness of an image captured by the imaging unit 20, in line with operation by a user and then variably sets the change rate of the brightness of the image. For example, a plurality of discrete values, namely, Low and High (>Low) may be selected as the change rate of the brightness of the image and the input unit 33 accepts input of the setting information specifying one of these values. The first embodiment will describe a case where the setting information variably setting the change rate of the brightness of the image is input to the control unit 34 when the change rate of the brightness of the image is altered to High from Low or altered to Low from High through operation on the input unit 33. The input unit 33 accepts input of patient data (e.g., an ID, a date of birth, and a name) regarding a particular patient serving as the subject and data such as examination details. The input unit 33 is an operation device such as a button or a touch panel provided on a front panel of the light source integrated processor 3. The input unit 33 may be implemented using an operation device such as a mouse and a keyboard connected to a main body section of the light source integrated processor 3. The input unit 33 may be a switch or the like provided on a grip section of the endoscope 2. The input unit 33 may be of a type where the instruction information is input thereto through remote operation from a portable terminal device such as a tablet type terminal device.

The control unit 34 is implemented using, for example, a CPU. The control unit 34 transfers the instruction information and data to respective components of the light source integrated processor 3, thereby controlling processing actions of respective constituent members of the light source integrated processor 3. While the endoscope 2 is mounted on the light source integrated processor 3, the control unit 34 is connected to the image sensor 22 of the endoscope 2 via the electric cable 24, thereby controlling these units. The control unit 34 includes a target range setting unit 341 and a clip level setting unit 342, which serve as a parameter setting unit to set a light adjustment parameter configured to enable the change rate of the brightness of the image to function variably such that the set change rate is obtained in line with the setting information variably setting the change rate of the brightness of the image captured by the imaging unit 20, which setting information has been input through the input unit 33.

The light adjustment parameter represents a target range of the brightness of the image continuously captured by the imaging unit 20 and the target range setting unit 341 sets the target range in accordance with the set change rate of the brightness of the image. The target range setting unit 341 sends target range information Ea indicating the set target range to the light adjustment unit 37. When the set change rate is faster than the change rate before setting, the target range setting unit 341 sets a narrower target range than the target range before setting, and conversely, when the set change rate is slower than the change rate before setting, the target range setting unit 341 sets a wider target range than the target range before setting.

Figure 2:
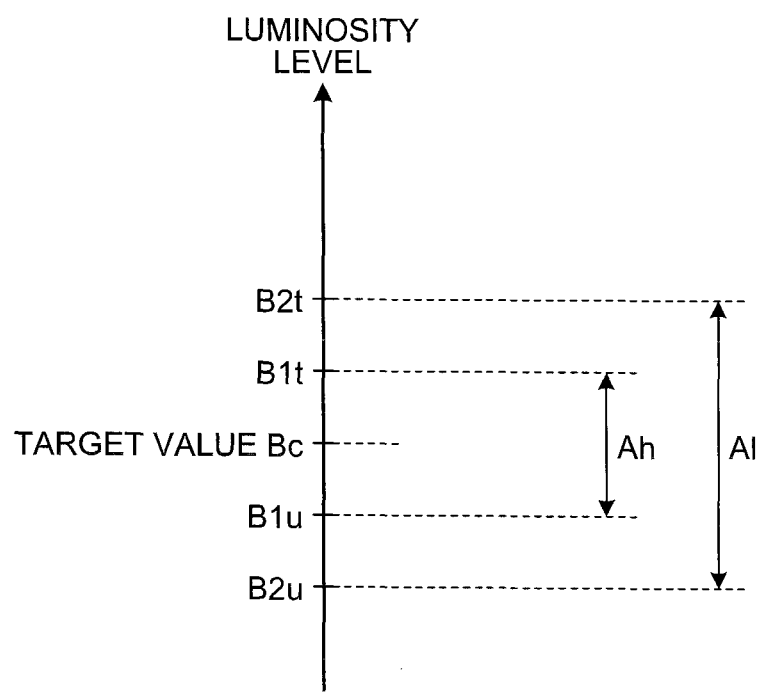
FIG. 2 is a diagram for explaining an example of a target range variably set by a target range setting unit illustrated in FIG. 1.

FIG. 2 is a diagram for explaining an example of the target range variably set by the target range setting unit 341. The target range setting unit 341 sets the target range such that the target range includes a predetermined target value Bc of an amount of brightness (luminosity level) of the image captured by the imaging unit 20. When the change rate of the brightness of the image is set to High, a range Ah in which an upper limit value is B1t and an lower limit value is B1u using the target value Bc as the center corresponds to the target range. When the change rate of the brightness of the image is set to Low, a range Al wider than a range Ah, in which an upper limit value is B2t (>B1t) and an lower limit value is B2u (<B1u) using the target value Bc as the center, corresponds to the target range. When the change rate of the brightness of the image is altered to High from Low, the target range setting unit 341 alters the target range to the range Ah from the range Al. When the change rate of the brightness of the image is altered to Low from High, the target range setting unit 341 alters the target range to the range Al from the range Ah.

The light adjustment parameter represents a clip level (deemed photometric value) selectable as an input value at the light adjustment unit 37 and the clip level setting unit 342 sets the clip level in accordance with the set change rate. The clip level setting unit 342 sends clip level information Ec indicating the set clip level to the clip processing unit 35. When the set change rate of the brightness of the image is faster than the change rate before setting, the clip level setting unit 342 sets a higher value than that of the clip level before setting as the clip level, and conversely, when the set change rate is slower than the change rate before setting, the clip level setting unit 342 sets a lower value than that of the clip level before setting as the clip level.

In the first embodiment, Dcl is set in advance as the clip level for the case where the change rate of the brightness of the image is set to Low, while Dch (>Dcl) is set in advance as the clip level for the case where the change rate of the brightness of the image is set to High. When the change rate of the brightness of the image is altered to High from Low, the clip level setting unit 342 alters the clip level to Dch from Dcl. When the change rate of the brightness of the image is altered to Low from High, the clip level setting unit 342 alters the clip level to Dcl from Dch.

Based on the clip level information Ec, the clip processing unit 35 associates the clip level Dc set by the clip level setting unit 342 with the luminosity signal Db input from the imaging unit 20 to output to the photometry unit 36.

The photometry unit 36 acquires a photometric value Mb indicating the luminosity level of the image captured by the image sensor 22 depending on the input luminosity signal Db. When the image signal (digital) is input, the photometry unit 36 may find the luminosity level from this image signal to acquire the photometric value Mb. The photometry unit 36 associates the clip level Dc with the photometric value Mb to output to the light adjustment unit 37.

The light adjustment unit 37 outputs, to the light source controller 38, a light adjustment control signal Cb configured to control the brightness of the image based on the photometric value Mb and the light adjustment parameter. The light adjustment unit 37 outputs the light adjustment control signal requiring the modification of the brightness of the image when the photometric value Mb acquired by the photometry unit 36 falls outside the target range indicated in the target range information Ea. The light adjustment unit 37 does not output the light adjustment control signal when the photometric value Mb acquired by the photometry unit 36 falls within the target range. Alternatively, the light adjustment unit 37 outputs the light adjustment control signal requiring no modification of the brightness of the image when the photometric value Mb acquired by the photometry unit 36 falls within the target range. Compared to a case where the range Al (refer to FIG. 2) serves as the target range (a case where the change rate of the brightness of the image is set to Low), when the range Ah narrower the range Al serves as the target range (a case where the change rate of the brightness of the image is set to High), the photometric value Mb is unlikely to fall within the target range. Accordingly, an output frequency of the light adjustment control signal from the light adjustment unit 37 increases and thus, a change in the brightness of the image is made faster. In contrast to this, when the range Al serves as the target range, the photometric value Mb is likely to fall within the target range, compared to a case where the range Ah serves as the target range. Accordingly, the output frequency of the light adjustment control signal from the light adjustment unit 37 decreases and thus, a change in the brightness of the image is made slower.

The light adjustment unit 37 generates the light adjustment control signal including a light adjustment control value in line with a light adjustment profile configured to enable an input value of the photometric value to reach a predetermined target value Bc of the brightness of the image captured by the imaging unit 20 within a certain time period. The light adjustment unit 37 selects one of the photometric value Mb and the clip level Dc as the input value based on a comparison result between the clip level Dc set by the clip level setting unit 342 and the photometric value Mb acquired by the photometry unit 36 and outputs the light adjustment control signal based on this input value and the light adjustment profile.

The light adjustment unit 37 selects the clip level Dc as the input value when the photometric value Mb is higher than the clip level Dc. In this case, the light adjustment unit 37 follows the light adjustment profile enabling the clip level Dc lower than the actual photometric value Mb to reach a predetermined target value within the certain time period and accordingly, a time period required for the actual photometric value Mb to reach the predetermined target value exceeds the certain time period, whereby a change in the brightness of the image is made slower from the viewpoint of appearance. The light adjustment unit 37 selects the photometric value Mb as the input value when the photometric value Mb is lower than the clip level Dc.

When Dcl serves as the clip level Dc (a case where the change rate of the brightness of the image is set to Low), the number of instances where the light adjustment unit 37 selects the clip level Dcl as the input value increases, compared to a case where Dch serves as the clip level Dc (a case where the change rate of the brightness of the image is set to High). Accordingly, when Dcl serves as the clip level Dc, a time period required for the actual photometric value Mb to reach the predetermined target value exceeds the certain time period in more instances than the case where Dch serves as the clip level Dc. As a consequence, a change in the brightness of the image is made slower from the viewpoint of appearance. When Dch serves as the clip level Dc, the number of instances where the light adjustment unit 37 selects the photometric value Mb as the input value increases, compared to a case where Dcl serves as the clip level Dc. Accordingly, when Dch serves as the clip level Dc, a time period required for the actual photometric value Mb to reach the predetermined target value falls within the certain time period in more instances than the case where Dcl serves as the clip level Dc. As a consequence, a change in the brightness of the image is made faster from the viewpoint of appearance. As described above, the light adjustment unit 37 selects the photometric value Mb or the clip level Dc as the input value to change the light adjustment profile to be applied when the light adjustment control value is generated, thereby altering the change rate of the brightness of the image. For example, when there is a larger difference between the input value and the predetermined target value, the light adjustment unit 37 is constituted by a lag-lead filter that sets a profile enabling the reaching in a shorter time period.

The light source controller 38 sets an amount of light emission (including intensity and a time) based on the light adjustment control signal Cb output by the light adjustment unit 37 and sends a control signal Cj to the light source unit 30 to cause the light source unit 30 to emit light by the set amount of light emission. With this, the light source unit 30 emits light having intensity set by the light source controller 38 during a set time.

The storage unit 39 is implemented using, for example, a volatile memory or a non-volatile memory and stores various programs for causing the light source integrated processor 3 to work. The storage unit 39 temporarily stores information obtained during processing by the light source integrated processor 3. The storage unit 39 stores the image signal and so on output from the endoscope 2. The storage unit 39 may be constituted using a memory card or the like mounted from the outside of the light source integrated processor 3.

The display device 4 is constituted using a display apparatus or the like employing a liquid crystal or an organic EL. The display device 4 displays various items of information including a display image output from the light source integrated processor 3.

Figure 3:
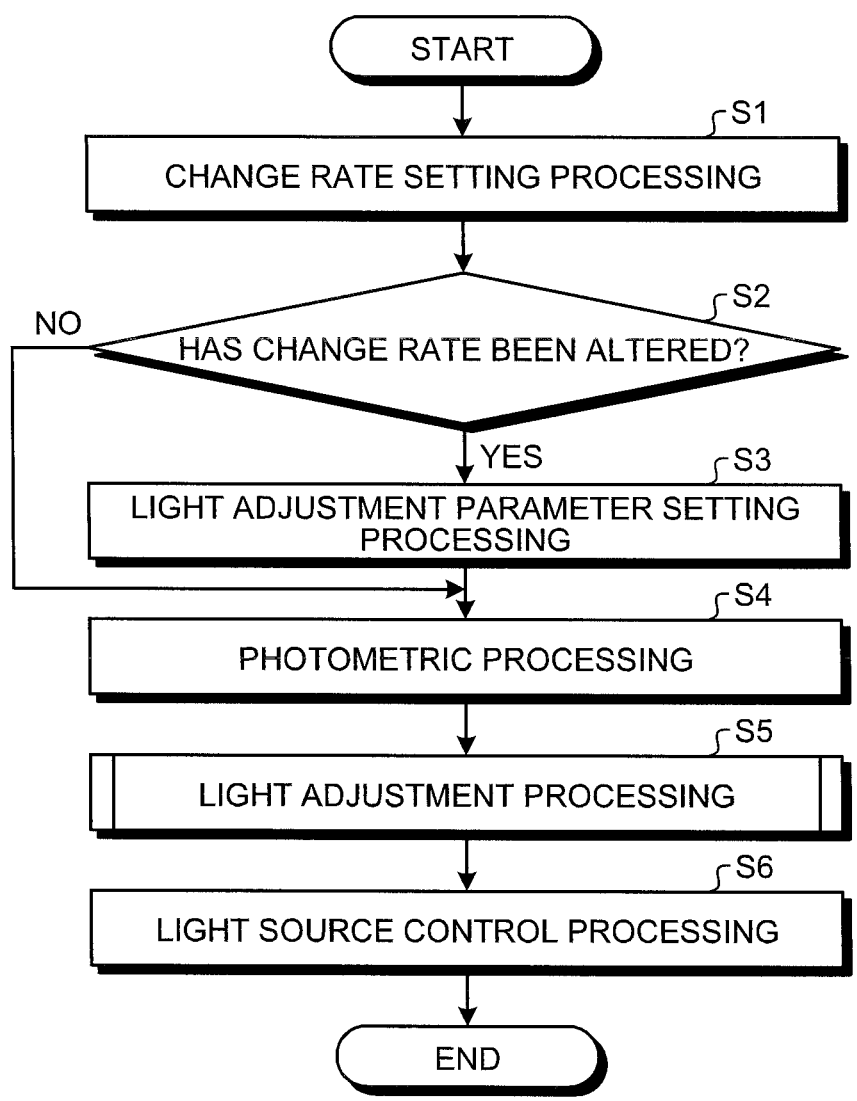
FIG. 3 is a flowchart illustrating processing procedures of light source control processing by a light source integrated processor illustrated in FIG. 1.

FIG. 3 is a flowchart illustrating processing procedures of light source control processing by the light source integrated processor 3. The light source control processing illustrated in FIG. 3 is carried out for each of frames.

As illustrated in FIG. 3, the input unit 33 carries out change rate setting processing to variably set the change rate of the brightness of the image captured by the imaging unit 20, in line with the setting information input through operation by the user (step S1). The control unit 34 judges whether the change rate of the brightness of the image has been altered, in line with the setting information input from the input unit 33 (step S2).

When the control unit 34 judges that the change rate of the brightness of the image has been altered (step S2: Yes), the target range setting unit 341 and the clip level setting unit 342 carry out light adjustment parameter setting processing to set a light adjustment parameter configured to enable the change rate of the brightness of the image to function variably such that the change rate set at step S1 is obtained (step S3). As described earlier, when the change rate of the brightness of the image is altered to High from Low, the target range setting unit 341 alters the target range to the range Ah from the range Al and the clip level setting unit 342 alters the clip level to Dch from Dcl. When the change rate of the brightness of the image is altered to Low from High, the target range setting unit 341 alters the target range to the range Al from the range Ah and the clip level setting unit 342 alters the clip level to Dcl from Dch.

When the control unit 34 judges that the change rate of the brightness of the image has not been altered (step S2: No) or after the light adjustment parameter setting processing at step S3, the photometry unit 36 carries out photometric processing to acquire the photometric value Mb indicating the luminosity level of the image captured by the imaging unit 20 (step S4).

The light adjustment unit 37 carries out light adjustment processing to output the light adjustment control signal configured to control the brightness of the image based on the photometric value Mb and the light adjustment parameter (step S5). The light source controller 38 carries out light source control processing to control the light source unit 30 such that the brightness of the image is modified based on the light adjustment control signal output by the light adjustment unit 37 (step S6). As a result, the amount of light emission from the light source unit 30 is altered and the brightness of the image is varied at the set change rate.

Figure 4:
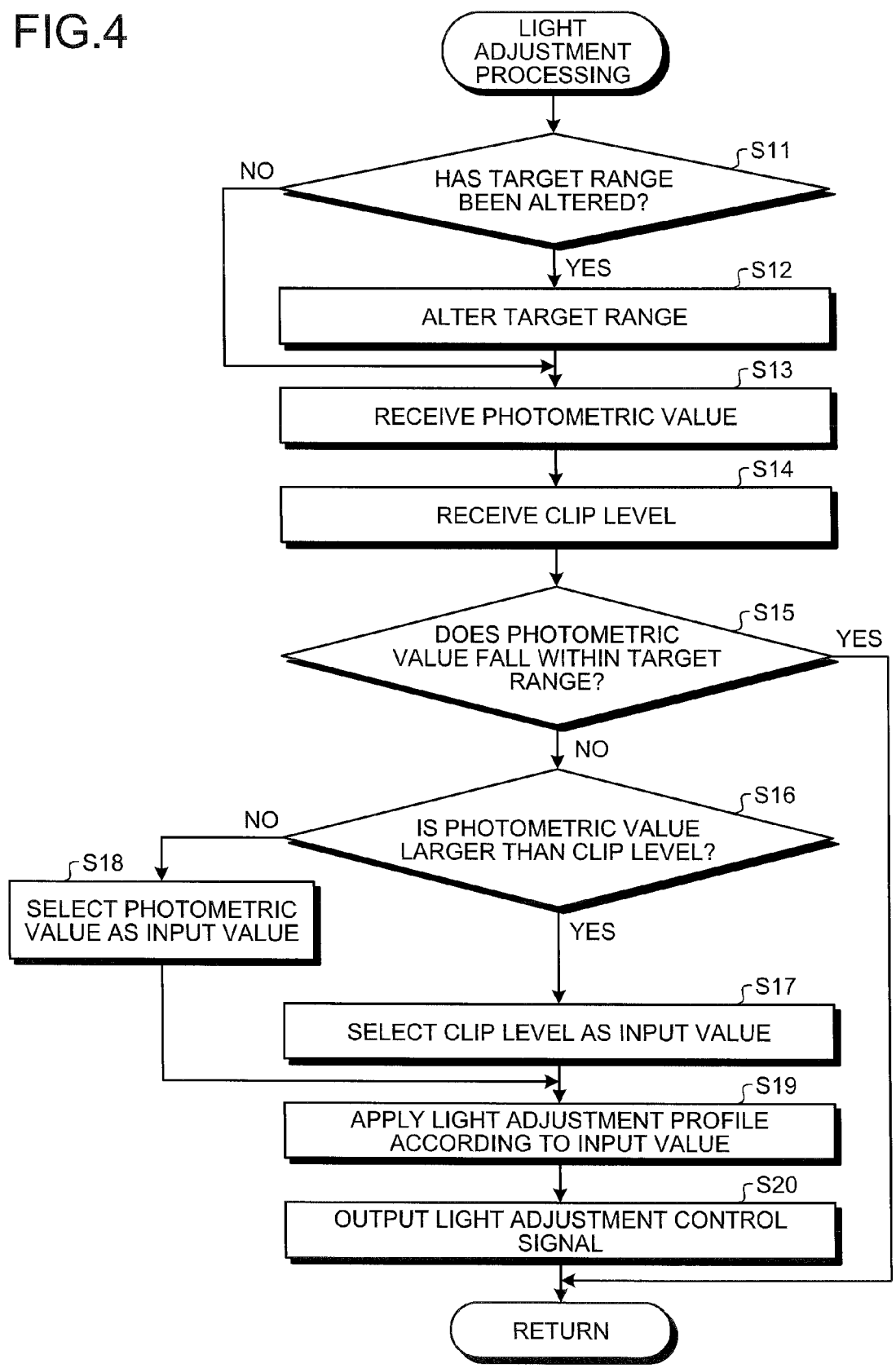
FIG. 4 is a flowchart illustrating processing procedures of light adjustment processing illustrated in FIG. 3.

FIG. 4 is a flowchart illustrating processing procedures of the light adjustment processing illustrated in FIG. 3. As illustrated in FIG. 4, the light adjustment unit 37 judges whether the target range of the brightness of the image has been altered, based on whether the target range information Ea sent from the target range setting unit 341 is present (step S11). When the light adjustment unit 37 judges that the target range of the brightness of the image has been altered (step S11: Yes), the light adjustment unit 37 alters the target range in line with the target range information Ea (step S12).

When the light adjustment unit 37 judges that the target range of the brightness of the image has not been altered (step S11: No) or after step S12 is completed, the light adjustment unit 37 receives the photometric value Mb from the photometry unit 36 (step S13) and also receives the clip level Dc associated with this received photometric value Mb (step S14).

The light adjustment unit 37 judges whether the received photometric value Mb falls within the target range (step S15). When the light adjustment unit 37 judges that the photometric value Mb falls within the target range (step S15: Yes), the light adjustment unit 37 terminates the light adjustment processing and does not output the light adjustment control signal. Alternatively, the light adjustment unit 37 outputs the light adjustment control signal requiring no modification of the brightness of the image. Accordingly, the light source controller 38 controls the light source unit 30 in line with the light adjustment control signal output for a preceding frame to the current frame. Therefore, the change rate for the preceding frame is kept as it is as the change rate of the brightness of the image.

On the other hand, when the light adjustment unit 37 judges that the photometric value Mb falls outside the target range (step S15: No), the light adjustment unit 37 carries out processing to output the light adjustment control signal. First, the light adjustment unit 37 compares the photometric value Mb and the clip level Dc with each other to judge whether the photometric value Mb is larger than the clip level Dc (step S16). When the light adjustment unit 37 judges that the photometric value Mb is larger than the clip level Dc (step S16: Yes), the light adjustment unit 37 selects the clip level Dc as the input value (step S17) and then proceeds to step S19. When the light adjustment unit 37 judges that the photometric value Mb is not larger than the clip level Dc (step S16: No), the light adjustment unit 37 selects the photometric value Mb as the input value (step S18) and then proceeds to step S19. The light adjustment unit 37 applies the light adjustment profile according to the input value (step S19) and then generates the light adjustment control signal Cb including the light adjustment control value to output (step S20).

Figure 5:
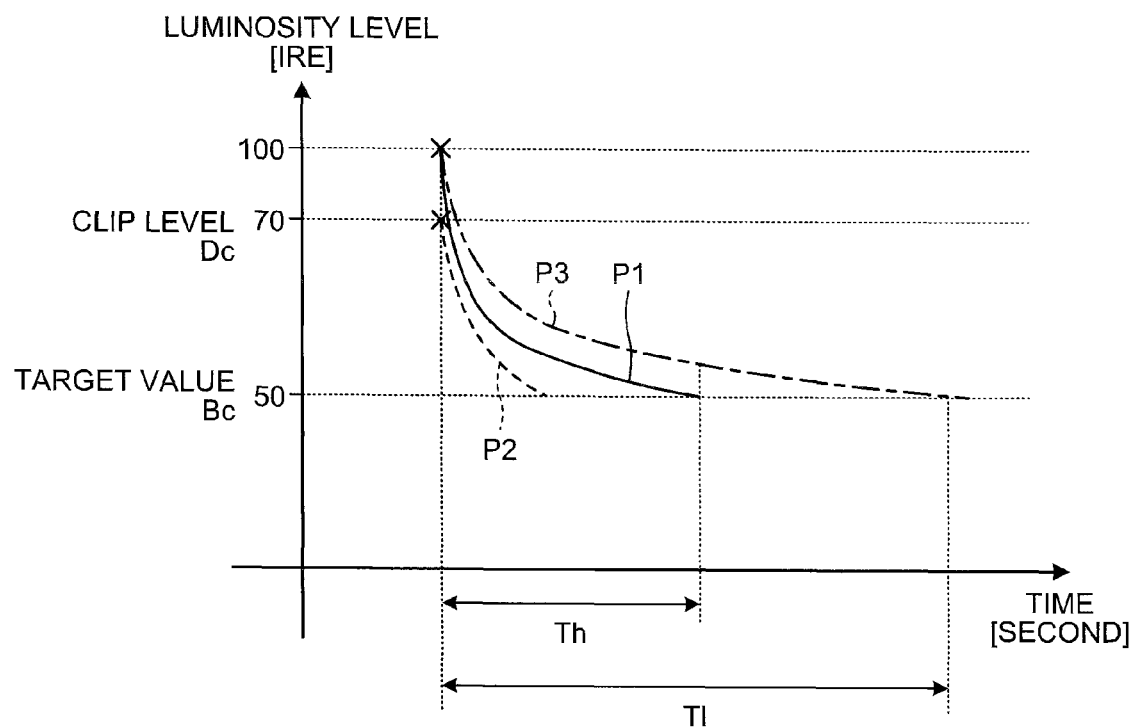
FIG. 5 is a diagram for explaining a light adjustment profile to be applied by a light adjustment unit illustrated in FIG. 1.

FIG. 5 is a diagram for explaining the light adjustment profile to be applied by the light adjustment unit 37. As illustrated in FIG. 5, the light adjustment unit 37 generates the light adjustment control value in line with the light adjustment profile configured to enable the input value to reach the predetermined target value Bc (e.g., 50 [IRE]) within a certain time period Th. For example, when the input value is 100 [IRE], the light adjustment unit 37 uses a light adjustment profile P1 enabling 100 [IRE] to reach the target value Bc within the time period Th. When the input value is 70 [IRE], the light adjustment unit 37 uses a light adjustment profile P2 enabling 70 [IRE] to reach the target value Bc within the time period Th. Because the light adjustment profile P2 has a small difference between the input value and the predetermined target value, compared to the case of the light adjustment profile P1, the light adjustment profile P2 draws a locus reaching the target value Bc more gently than the case of the light adjustment profile P1.

To give an example, a case where the clip level Dc is 70 [IRE] and the actual photometric value Mb is 100 [IRE] will be described. In this case, the light adjustment unit 37 selects the clip level Dc as the input value (step S17) since the photometric value Mb is higher than the clip level Dc (step S16: Yes) and then applies the light adjustment profile P2 enabling 70 [IRE] to reach the predetermined target value within the certain time period (step S19). Thereafter, the light adjustment unit 37 generates the light adjustment control signal including the light adjustment control value to output (step S20). The actual brightness of the image at this time corresponds to the photometric value Mb, specifically, 100 [IRE] and accordingly, the brightness of the image is varied in line with a light adjustment profile P3 in which the luminosity level decreases from 100 [IRE], while using the locus of the light adjustment profile P2 in which the luminosity level decreases from 70 [IRE] as it is. As a result, a time period Tl required for the actual photometric value Mb (100 [IRE]) to reach the predetermined target value Bc (50 [IRE]) exceeds the time period Th and thus, a change in the brightness of the image is made slower from the viewpoint of appearance.

In the first embodiment, for example, the clip level Dcl when the change rate of the brightness of the image is set to Low is set to 70 [IRE], whereas the clip level Dch when the change rate of the brightness of the image is set to High is set to the same value as a saturation value of the luminosity level. When the change rate of the brightness of the image is set to Low, the number of instances where the light adjustment unit 37 selects the clip level Dcl as the input value increases, compared to a case where the photometric value Mb is input to a filter as it is (a case where the change rate of the brightness of the image is set to High). Accordingly, when the change rate of the brightness of the image is set to Low, a time period required for the actual photometric value Mb to reach the predetermined target value Bc exceeds the certain time period and thus, a change in the brightness of the image is made slower from the viewpoint of appearance.

As described thus far, the first embodiment solely changes the target range and the clip level Dc of the brightness of the image required for the light adjustment processing in accordance with the change rate of the brightness of the image, thereby altering the change rate of the brightness of the image. Consequently, according to the first embodiment, the change rate of the brightness of the image may be altered only by carrying out simple processing of changing the light adjustment parameter required for the light adjustment processing, while using an uncomplicated configuration as it is without particularly providing a plurality of photometric circuits.

Note that, although the first embodiment has described an example where two levels of the rates, namely, Low and High are set as the change rates of the brightness of the image, as a matter of course, the change rates are not limited to the two levels and a configuration allowing a more number of levels to be set may be employed. In addition, the change rate of the brightness of the image may be altered and set through operation by the user on the input unit 33, for example, through operation to input a numerical value of the actual change rate or operation to set using a slider bar displayed on a screen of the display device 4, with which the change rates are associated.

Meanwhile, the change rate of the brightness of the image is not limited to the case where the alteration thereof is set in response to operation by the user on the input unit 33 but may be configured in such a manner that the alteration thereof is set in response to a photometric mode to be set (peak photometry or average photometry) or the like. For example, in the case of a peak photometric mode, the control unit 34 sets the change rate of the brightness of the image to High in order to enhance an object tracking characteristic of the brightness. In the case of an average photometric mode, the control unit 34 sets the change rate of the brightness of the image to Low in order to prevent difficulties in working out an average value due to frequent fluctuations in the brightness of the image.

Additionally, the change rate of the brightness of the image is not limited to the alteration by way of light source control that variably controls the amount of light emission of the light source unit 30 but the alteration may be by way of variable control of an exposure time through electronic shutter control of the image sensor 22. Alternatively, both of the light source control and the exposure time control may be employed.

First Variation of First Embodiment

Figure 6:
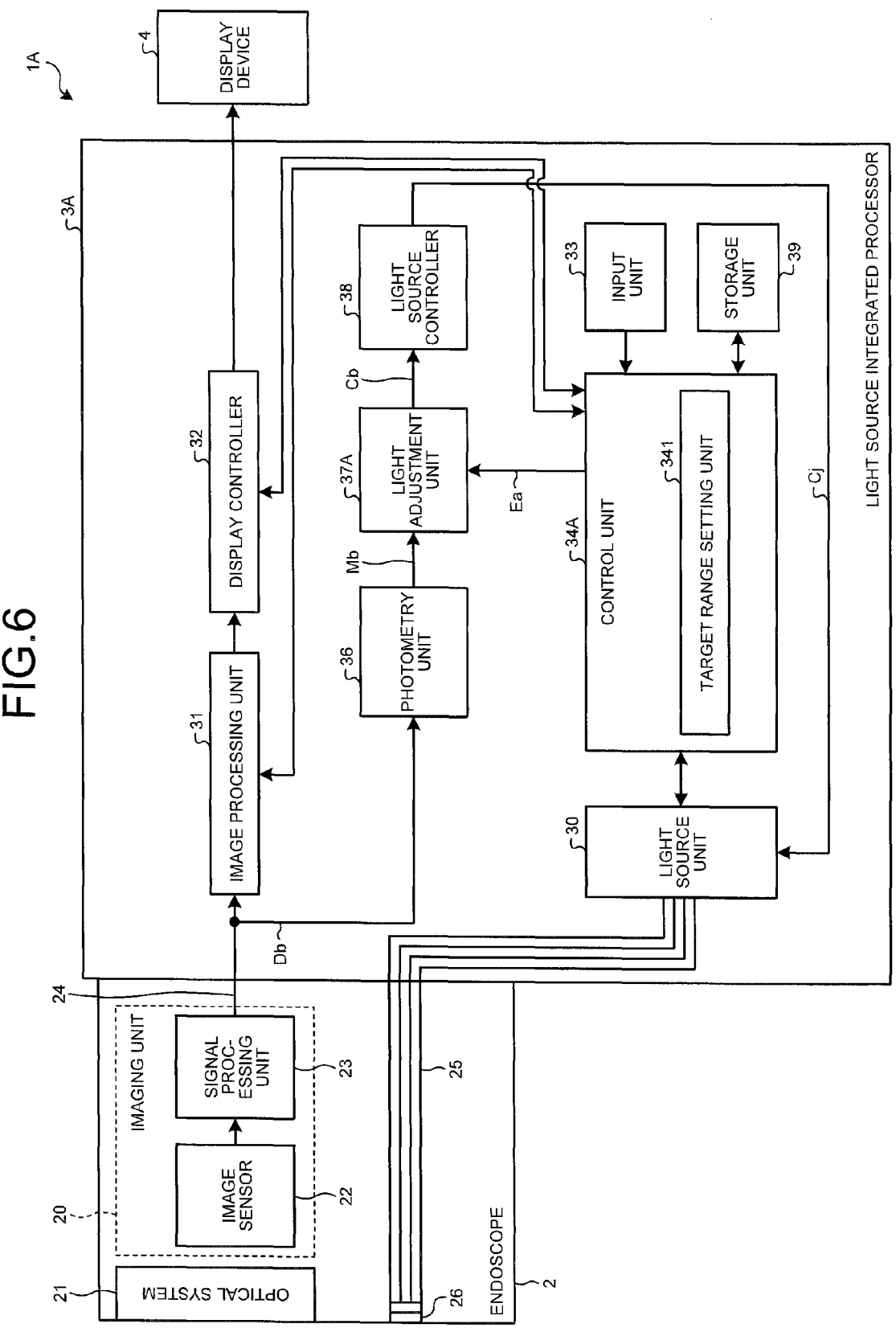
FIG. 6 is a schematic diagram illustrating an overview configuration of an endoscope system according to a first variation of the first embodiment.

FIG. 6 is a schematic diagram illustrating an overview configuration of an endoscope system according to a first variation of the first embodiment.

When compared with the configuration illustrated in FIG. 1, a light source integrated processor 3A in an endoscope system 1A illustrated in FIG. 6 has a configuration obtained by removing the clip processing unit 35 therefrom, while including a control unit 34A having a configuration obtained by removing the clip level setting unit 342 therefrom and a light adjustment unit 37A. Accordingly, in the endoscope system 1A, a target range setting unit 341 variably sets the target range of the brightness of the image during the light adjustment parameter setting processing (step S3 in FIG. 3). The light adjustment unit 37A carries out the light adjustment processing in line with the target range of the brightness of the image for which the target range setting unit 341 has altered a setting. Specifically, the light adjustment unit 37A carries out processing from step S11 to step S13 and at step S15, step S19, and step S20 illustrated in FIG. 4 when carrying out the light adjustment processing.

Also when the target range setting unit 341 variably sets the size of the target range as the light adjustment parameter in accordance with the change rate of the brightness of the image as in the first variation of the first embodiment, the output frequency of the light adjustment control signal from the light adjustment unit 37A is changed, whereby an apparent change rate of the brightness of the image is altered.

Second Variation of First Embodiment

Figure 7:
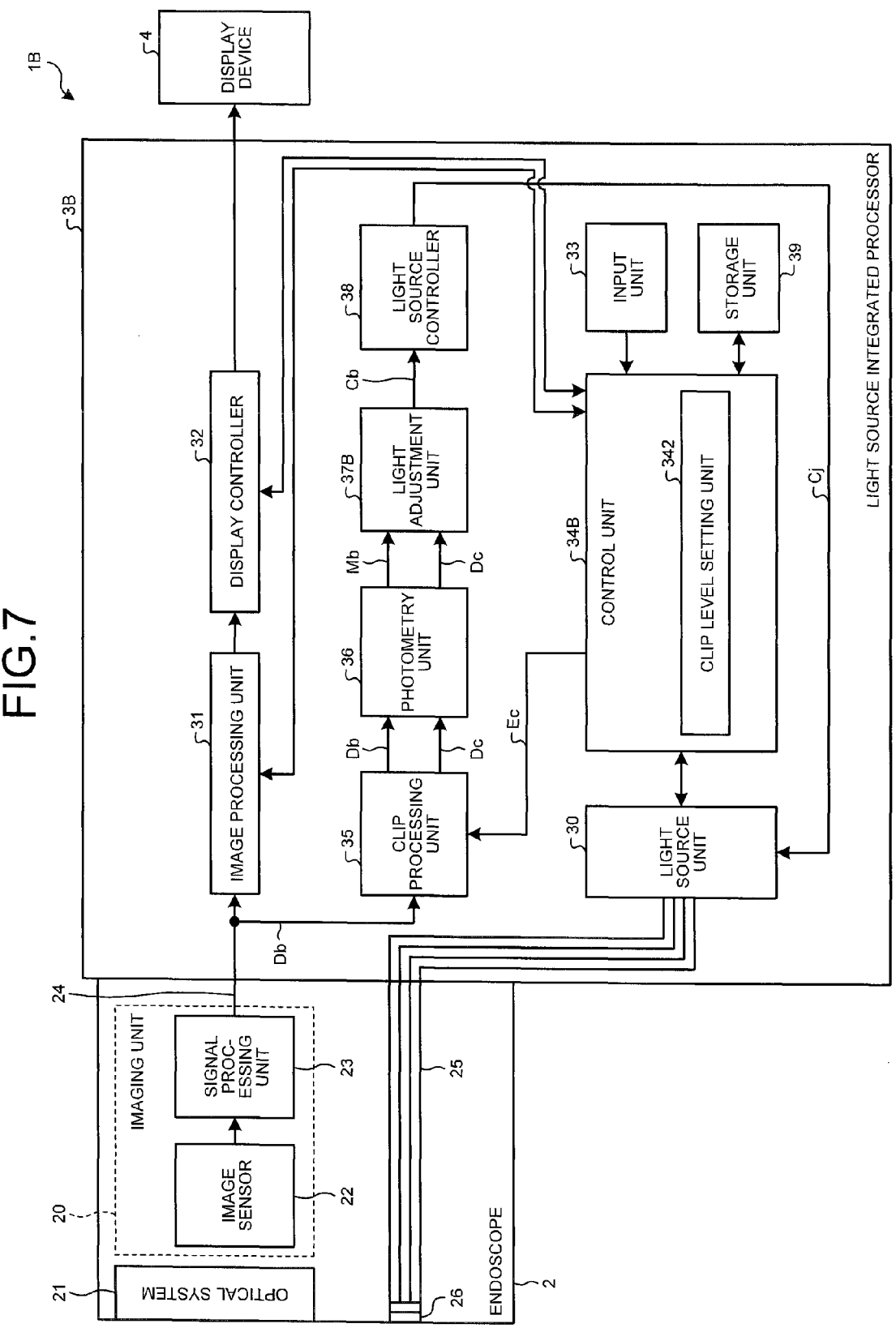
FIG. 7 is a schematic diagram illustrating an overview configuration of an endoscope system according to a second variation of the first embodiment.

FIG. 7 is a schematic diagram illustrating an overview configuration of an endoscope system according to a second variation of the first embodiment.

When compared with the configuration illustrated in FIG. 1, a light source integrated processor 3B in an endoscope system 1B illustrated in FIG. 7 includes a control unit 34B having a configuration obtained by removing the target range setting unit 341 therefrom and a light adjustment unit 37B. In the endoscope system 1B, a clip level setting unit 342 variably sets the clip level during the light adjustment parameter setting processing (step S3 in FIG. 3). The light adjustment unit 37B sets the input value based on the clip level set by the clip level setting unit 342 and a comparison result with the photometric value supplied by a photometry unit 36. Specifically, the light adjustment unit 37B carries out processing from step S13 to step S20 illustrated in FIG. 4 when carrying out the light adjustment processing.

Also when the clip level setting unit 342 variably sets the clip level as the light adjustment parameter as in the second variation of the first embodiment, the light adjustment profile to be applied by the light adjustment unit 37B is changed, whereby an apparent change rate of the brightness of the image is altered.

Second Embodiment

Figure 8:
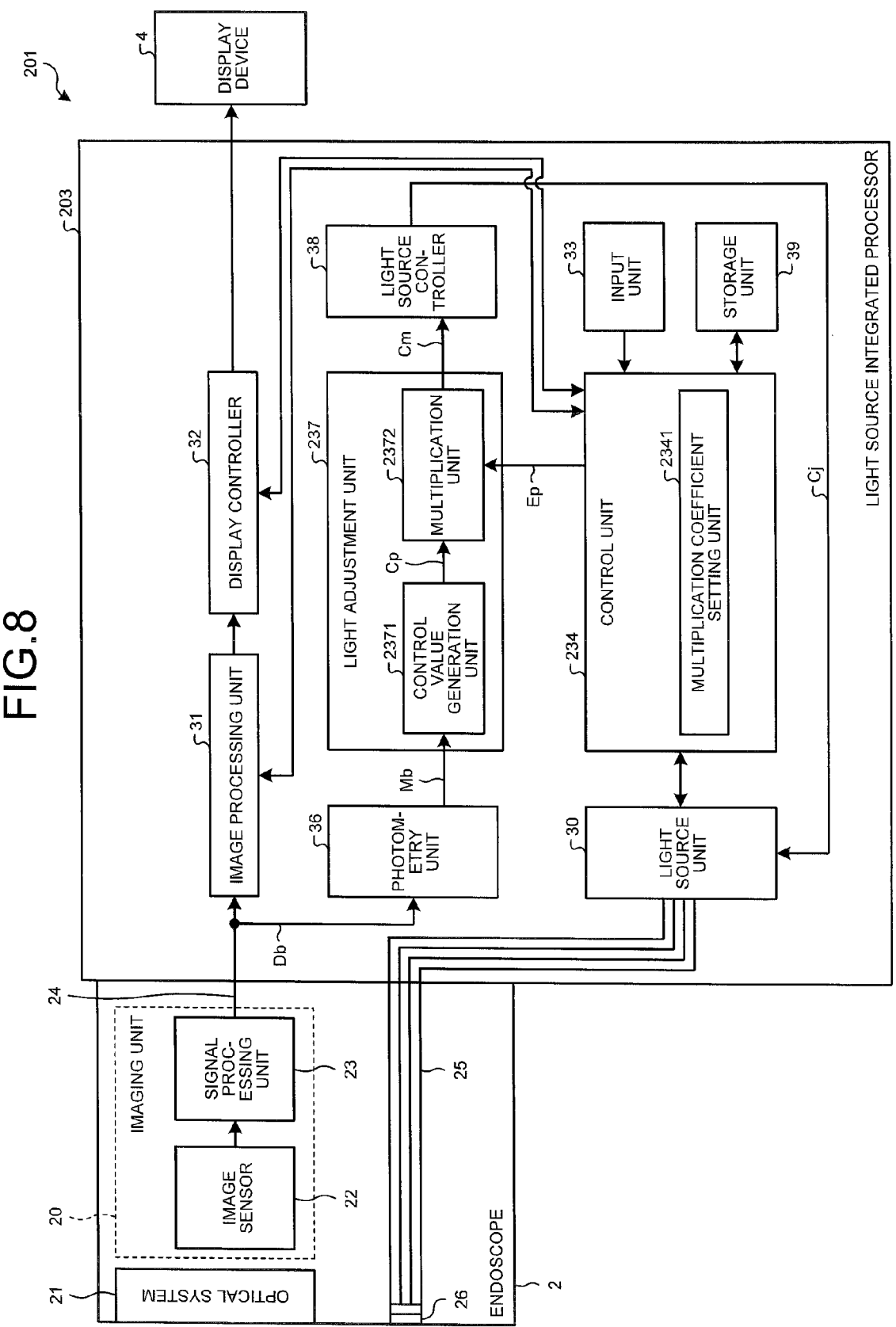
FIG. 8 is a schematic diagram illustrating an overview configuration of an endoscope system according to a second embodiment.

Next, a second embodiment will be described. FIG. 8 is a schematic diagram illustrating an overview configuration of an endoscope system according to a second embodiment.

When compared with the light source integrated processor 3 illustrated in FIG. 1, a light source integrated processor 203 in the endoscope system 201 illustrated in FIG. 8 has a configuration obtained by removing the clip processing unit 35 therefrom. The light source integrated processor 203 has a configuration including a control unit 234 having a multiplication coefficient setting unit 2341 and a light adjustment unit 237 having a control value generation unit 2371 and a multiplication unit 2372.

The control unit 234 has a similar function as that of the control unit 34 illustrated in FIG. 1. The multiplication coefficient setting unit 2341 sets a multiplication coefficient (change rate coefficient) according to the change rate set by an input unit 33 and then outputs, to the multiplication unit 2372, an multiplication coefficient Ep that has been set. The multiplication coefficient setting unit 2341 sets a larger value as the multiplication coefficient Ep when a faster change rate is used for the brightness of the image. The multiplication coefficient setting unit 2341 sets the multiplication coefficient Ep for a case where the change rate of the brightness of the image is set to High such that a value larger than the multiplication coefficient Ep when the change rate of the brightness of the image is set to Low is obtained.

The control value generation unit 2371 generates a light adjustment control value Cp to control the brightness of the image based on the photometric value Mb acquired by a photometry unit 36. As in the light adjustment unit 37 illustrated in FIG. 1, the control value generation unit 2371 generates the light adjustment control value Cp in line with the light adjustment profile configured to enable the photometric value Mb serving as the input value to reach a predetermined target value for the brightness of the image captured by an imaging unit 20 within a certain time period.

The multiplication unit 2372 multiplies the light adjustment control value Cp generated by the control value generation unit 2371 by at least the multiplication coefficient Ep set by the multiplication coefficient setting unit 2341 and then outputs a light adjustment control signal Cm including the resultant multiplied value to a light source controller 38. A larger value of the multiplication coefficient Ep is set when a faster change rate is used for the brightness of the image. Accordingly, a larger coefficient is multiplied to the light adjustment control value Cp when a faster change rate is used for the brightness of the image and thus, a light adjustment control characteristic forms a steeper slope relative to time. Consequently, the change rate of the brightness of the image is made faster. The light adjustment unit 237 carries out computational processing of multiplying the light adjustment control value Cp generated by the control value generation unit 2371 by at least the multiplication coefficient Ep, thereby adjusting the light adjustment control value in the light adjustment control signal Cm to be actually output to the light source controller 38 such that a value corresponding to the change rate for the brightness of the image is obtained.

The light source integrated processor 203 carries out processing procedures similar to the respective processing procedures illustrated in FIG. 3 as the light source control processing. However, the multiplication coefficient setting unit 2341 variably sets the multiplication coefficient Ep according to the change rate for the brightness of the image set by the input unit 33 as the light adjustment parameter setting processing (step S3).

FIG. 9 is a flowchart illustrating processing procedures of light adjustment processing carried out by the light adjustment unit 237 illustrated in FIG. 8. As illustrated in FIG. 9, the light adjustment unit 237 receives the multiplication coefficient Ep from the multiplication coefficient setting unit 2341 (step S21). Step S22 illustrated in FIG. 9 corresponds to step S13 illustrated in FIG. 4.

The control value generation unit 2371 judges whether the received photometric value Mb falls within the target range (step S23). Note that, as described in the first embodiment, the target range also may be variably set through operation on the input unit 33. When the control value generation unit 2371 judges that the photometric value Mb falls within the target range (step S23: Yes), the control value generation unit 2371 terminates the light adjustment processing.

On the other hand, when the control value generation unit 2371 judges that the photometric value Mb falls outside the target range (step S23: No), the control value generation unit 2371 applies the light adjustment profile according to the photometric value Mb serving as the input value (step S24) and then generates the light adjustment control value Cp (step S25). The multiplication unit 2372 multiplies the light adjustment control value Cp generated by the control value generation unit 2371 by at least the multiplication coefficient Ep (step S26) and then outputs the light adjustment control signal Cm including a value obtained from the multiplication to the light source controller 38 (step S27). For example, the multiplication unit 2372 carries out computational processing indicated below at step S26 to acquire the light adjustment control value included in the light adjustment control signal Cm.

Light adjustment control value=(light adjustment control value $Cp \times$(target value $Bc$/photometric value $Mb$))$\times$multiplication coefficient $Ep$ As in this second embodiment, by carrying out computational processing of multiplying the light adjustment control value Cp generated by the control value generation unit 2371 by at least the multiplication coefficient Ep corresponding to the change rate for the brightness of the image, the light adjustment control value in the light adjustment control signal Cm to be actually output to the light source controller 38 may be adjusted such that a value corresponding to the change rate of the brightness of the image is obtained.

In addition, a light source of the light source unit 30 may be configured to use a plurality of LEDs that emit light in different wavelength bands from one another (e.g., a red LED, a green LED, and a blue LED) and multiplex light emitting from the respective LEDs such that a desired color tone of the illumination light is obtained. Meanwhile, the light source unit 30 may adopt a configuration using a sequential lighting in which light having different color components is emitted in time series. Alternatively, the light source unit 30 may be of a type using a laser light source. Alternatively, the light source unit 30 may have a configuration including a light source such as a xenon lamp or a halogen lamp and a light source control component that controls an optical filter, a diaphragm, and respective members of the light source unit 30.

Additionally, although the first and second embodiments have described the light source integrated processors 3, 3A, 3B, and 203 in which light sources are integrated as examples, it is apparent that the embodiments may be similarly applied to a case where a processor and a light source device are provided as separate bodies.

Furthermore, a signal sent and received between the endoscope 2 and each of the light source integrated processors 3, 3A, 3B, and 203 in the first and second embodiments is not limited to an electrical signal but may be an optical signal obtained by converting the electrical signal. In this case, a transmission path for the optical signal such as an optical fiber is used to transmit the optical signal between the endoscope 2 and each of the light source integrated processors 3, 3A, 3B, and 203. As a matter of course, wireless communication may be used in addition to wired communication to send and receive the signal between the endoscope 2 and each of the light source integrated processors 3, 3A, 3B, and 203.

The first and second embodiments have described the endoscope system utilizing the endoscope including the flexible insertion portion. However, as a matter of course, an endoscope system utilizing an endoscope including a hard insertion portion may be employed. In addition, the endoscope may be equipped with a light source and a control function for controlling the image sensor and the light source. In this case, the light source is not limited to a type where the light source is configured as a separate body from the endoscope but may be a semiconductor light source or the like provided at the distal end of the insertion portion of the endoscope. Meanwhile, the configuration is not limited to one in which the image sensor is provided at the distal end of the insertion portion of the endoscope. For example, the image sensor may be configured in such a manner as to be provided at a proximal end of the insertion portion such that an optical image transmitted from the distal end to the proximal end of the insertion portion through an optical fiber is captured. Furthermore, the endoscope is not limited to one including the image sensor provided at the distal end of the insertion portion but a configuration for connecting an eyepiece camera head of an optical endoscope such as a fiber scope or an optical viewing tube may be employed.

When the semiconductor light source is used as the light source, the brightness of emission light is controlled using at least one of emission time control of the illumination light from the light source through pulse width modulation (PWM) control and illumination intensity control through amplitude control of an electric current value driving the semiconductor light source (pulse amplitude modulation (PAM)). As a matter of course, both of the above-mentioned control techniques may be used together, or alternatively, pulse number modulation (PNM) control that controls the number of emission pulses, or the like may be further used together. Meanwhile, when a lamp is used as the light source, the brightness of emission light is controlled by controlling the degree of aperture of a diaphragm member mechanically limiting the amount of the illumination light emitting from the lamp.

In addition, although the endoscope systems 1, 1A, 1B, and 201 for medical use have been exemplified as the embodiments in the description, it is apparent that the embodiments also may be applied to an endoscope system for industrial use.

Furthermore, execution programs corresponding to the respective processing procedures carried out by the light source integrated processors 3, 3A, 3B, and 203 according to the embodiments may be configured so as to be provided by being recorded in a recording medium readable by a computer, such as a CD-ROM, a flexible disk, a CD-R, and a DVD, as a file in an installable format or in an executable format, or alternatively, may be configured so as to be saved and kept in a computer connected to a network such as the Internet such that the provision thereof is by way of download via the network.

According to the disclosure, only by carrying out simple processing of setting the light adjustment parameter configured to cause the change rate of the brightness of the image to function variably such that the set change rate is obtained, outputting the light adjustment control signal configured to control the brightness of the image based on the photometric value indicating the brightness of the image continuously captured by the imaging unit and the light adjustment parameter, and then varying the brightness of the image based on the light adjustment control signal, it is made possible to alter the change rate of the brightness of the image using an uncomplicated configuration as it is.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging system comprising:
   an imaging unit configured to continuously capture an image;
   a photometry unit configured to acquire a photometric value indicating the brightness of the image continuously captured by the imaging unit;
   a change rate setting unit configured to variably set a change rate of brightness of the image continuously captured by the imaging unit the change rate being defined as a rate at which the photometric value acquired by the photometry unit reaches a predetermined target value of brightness;
   a parameter setting unit configured to be capable of variably setting a light adjustment parameter for altering the change rate of the brightness of the image in accordance with the change rate set by the change rate setting unit so as to include the predetermined target value of the brightness of the image continuously captured by the imaging unit; and
   a light adjustment unit configured to generate, based on the photometric value input from the photometry unit, a light adjustment control signal in line with a light adjustment profile for causing the photometric value input from the photometry unit to reach a predetermined target value of the brightness of the image captured by the imaging unit within a certain time period,
   wherein the parameter setting unit is configured to set a deemed photometric value as the light adjustment parameter, and
   wherein the light adjustment unit is configured to select one of the photometric value and the deemed photometric value as an input value of the photometric value based on a comparison result between the deemed photometric value set by the parameter setting unit and the photometric value acquired by the photometry unit, and outputs the light adjustment control signal based on the input value and the light adjustment profile.

2. The imaging system according to claim 1, further comprising:
   a light source unit configured to emit illumination light; and
   a light source controller configured to alter the change rate of the brightness of the image to the change rate set by the change rate setting unit by variably controlling an amount of light emission from the light source unit based on the light adjustment control signal.

3. The imaging system according to claim 1,
   wherein the light adjustment unit is configured to output the light adjustment control signal for modifying the brightness of the image when the photometric value acquired by the photometry unit falls outside the target range and to output the light adjustment control signal for not modifying the brightness of the image when the photometric value acquired by the photometry unit falls within the target range.

4. The imaging system according to claim 3, wherein the parameter setting unit sets a narrower target range than the target range before setting when the change rate set by the change rate setting unit is faster than the change rate before setting, the parameter setting unit sets a wider target range than the target range before setting when the change rate set by the change rate setting unit is slower than the change rate before setting.

5. The imaging system according to claim 1, wherein the light adjustment unit selects the deemed photometric value as the input value when the photometric value is higher than the deemed photometric value and selects the photometric value as the input value when the photometric value is lower than the deemed photometric value.

6. The imaging system according to claim 1, wherein the parameter setting unit sets a higher value than the deemed photometric value before setting as the deemed photometric value when the change rate set by the change rate setting unit is faster than the change rate before setting, and the parameter setting unit sets a lower value than the deemed photometric value before setting as the deemed photometric value when the change rate set by the change rate setting unit is slower than the change rate before setting.

7. The imaging system according to claim 1, wherein
the light adjustment parameter includes the target range of the brightness of the image continuously captured by the imaging unit and the deemed photometric value,
the parameter setting unit sets the target range in accordance with the change rate set by the change rate setting unit, while variably setting the deemed photometric value in accordance with the change rate set by the change rate setting unit, and
the light adjustment unit selects one of the photometric value and the deemed photometric value as an input value of the photometric value input from the photometry unit based on a comparison result between the deemed photometric value set by the parameter setting unit and the photometric value acquired by the photometry unit to output the light adjustment control signal based on the input value and the light adjustment profile when the photometric value acquired by the photometry unit falls outside the target range, and outputs the light adjustment control signal for not modifying the brightness of the image when the photometric value acquired by the photometry unit falls within the target range.

8. An imaging system comprising:
an imaging unit configured to continuously capture an image;
a photometry unit configured to acquire a photometric value indicating the brightness of the image continuously captured by the imaging unit;
a change rate setting unit configured to variably set a change rate of brightness of the image continuously captured by the imaging unit, the change rate being defined as a rate at which the photometric value acquired by the photometry unit reaches a predetermined target value of brightness;
a parameter setting unit configured to a light adjustment parameter for altering the change rate of the brightness of the image in accordance with a change rate coefficient according to the change rate set by the change rate setting unit so as to include the predetermined target value of the brightness of the image continuously captured by the imaging unit;
a light adjustment unit configured to multiply a value of the light adjustment control signal generated in line with a light adjustment profile for causing the photometric value input from the photometry unit to reach a predetermined target value of the brightness of the image captured by the imaging unit within a certain time period, by the change rate coefficient set by the parameter setting unit, to output based on the photometric value input from the photometry unit.

9. A processing device for processing an image continuously captured by an imaging unit, the processing device comprising:
a photometry unit configured to acquire a photometric value indicating the brightness of the image continuously captured by the imaging unit;
a change rate setting unit configured to variably set a change rate of brightness of the image continuously captured by the imaging unit the change rate being defined as a rate at which the photometric value acquired by the photometry unit reaches a predetermined target value of brightness;
a parameter setting unit configured to be capable of variably setting a light adjustment parameter for altering the change rate of the brightness of the image in accordance with the change rate set by the change rate setting unit so as to include the predetermined target value of the brightness of the image continuously captured by the imaging unit; and
a light adjustment unit configured to generate, based on the photometric value input from the photometry unit, a light adjustment control signal in line with a light adjustment profile for causing the photometric value input from the photometry unit to reach a predetermined target value of the brightness of the image captured by the imaging unit within a certain time period,
wherein the parameter setting unit sets a deemed photometric value as the light adjustment parameter, and
wherein the light adjustment unit is configured to select one of the photometric value and the deemed photometric value as an input value of the photometric value based on a comparison result between the deemed photometric value set by the parameter setting unit and the photometric value acquired by the photometry unit, and to output the light adjustment control signal based on the input value and the light adjustment profile.

* * * * *